United States Patent [19]

Kostas

[11] Patent Number: 5,491,249
[45] Date of Patent: Feb. 13, 1996

[54] PROCESS FOR PREPARING CYCLIC POLYSILOXANES FROM LINEAR POLYSILOXANES

[75] Inventor: John N. Kostas, Claymont, Del.

[73] Assignee: Hercules Incorporated, Wilmington, Del.

[21] Appl. No.: 425,542

[22] Filed: Apr. 20, 1995

[51] Int. Cl.$^6$ ............................................. C07F 7/08
[52] U.S. Cl. ............................................. 556/460; 556/461
[58] Field of Search ............................................. 556/460, 461

[56] References Cited

U.S. PATENT DOCUMENTS

| | | | |
|---|---|---|---|
| 3,558,681 | 1/1971 | Kuznetsova et al. | 260/448.2 |
| 3,714,213 | 1/1973 | Miller et al. | 260/448.2 E |
| 3,989,733 | 11/1976 | Okamoto et al. | 556/460 |
| 4,111,973 | 9/1978 | Bluestein | 556/460 |
| 4,276,425 | 6/1981 | Burkhardt et al. | 556/460 |
| 4,895,967 | 1/1990 | Crivello et al. | 556/460 X |
| 5,110,972 | 5/1992 | Greenlee | 556/460 |
| 5,247,116 | 9/1993 | Buese et al. | 556/461 X |
| 5,420,325 | 5/1995 | Razzano | 556/460 |

OTHER PUBLICATIONS

Hunter, et al., *Journal of The American Chemical Society*, 68, 667 (1946).

J. V. Crivello, et al., "Synthesis of Cyclic Siloxanes by the Thermal Depolymerization of Linear Poly(siloxanes)", *Chemistry of Materials*, 1989, vol. 1, pp. 445–451.

*Primary Examiner*—Paul F. Shaver
*Attorney, Agent, or Firm*—Robert P. O'Flynn O'Brien

[57] ABSTRACT

Cyclic polysiloxanes are produced by continuously passing a feed comprising linear polysiloxanes through a reactor containing a solid acidic catalyst at a pressure greater than one atmosphere under an inert atmosphere to produce a mixture comprising volatile cyclic polysiloxanes, nonvolatile reaction products, and unreacted linear polysiloxanes. The volatile products can then be recovered, and the nonvolatile reaction products and unreacted linear polysiloxanes can be added to the linear polysiloxane feed to form a recycle stream that is passed back through the reactor. Recycling increases the yield of the desired cyclic species.

37 Claims, 1 Drawing Sheet

PROCESS FOR PREPARING CYCLIC POLYSILOXANES FROM LINEAR POLYSILOXANES

This invention relates to a process for preparing cyclic polysiloxanes from linear polysiloxanes.

BACKGROUND OF THE INVENTION

Commercial siloxane polymers are generally produced by the hydrolysis of dichlorosilanes, yielding a mixture of cyclic and linear polysiloxanes. The production of cyclic polysiloxanes can be enhanced relative to linear polysiloxanes by performing the hydrolysis in a highly dilute solution, which improves the probability of cyclization versus oligomerization.

The preparation of poly(organohydrosiloxanes) is of particular interest due to the reactivity of the silicon-hydrogen bond. Organosilicon compounds can be produced by reaction of olefins with the ≡SiH groups. The production of cyclic poly(organohydrosiloxanes), however, is especially difficult via the hydrolysis reaction due to the high reactivity of the silicon-hydrogen bond.

Several methods other than hydrolysis have been reported to produce cyclic polysiloxanes. Most prior processes involve the base-catalyzed thermal cracking of poly(diorganosiloxanes). Cyclic polysiloxanes have been prepared by Hunter et al., *Journal of the American Chemical Society*, 68, 667, (1946) via the cracking of linear polysiloxanes in the presence of a base catalyst, such as sodium hydroxide. Okamato et al., U.S. Pat. No. 3,989,733, describe a process for the thermal cracking of poly(diorganosiloxanes) in the presence of lithium hydroxide to produce cyclic poly(diorganosiloxanes). A process for the catalyzed cracking of silicone polymers is disclosed by Greenlee, U.S. Pat. No. 5,110,972. High molecular weight silicone polymers are dissolved in an organic solvent containing sulfuric acid at 150°–180° C., and cracked to lower molecular weight linear species. This is followed by the addition of potassium hydroxide and the distillation of the cyclic products from the solution. Kuznetsova et al., U.S. Pat. No. 3,558,681, describe the preparation of methylphenylcyclotri- and tetrasiloxanes by the vapor phase rearrangement of the linear siloxane at 250°–360° C. using lithium hydroxide or lithium silanolate as the catalyst. While cyclic poly(diorganosiloxanes) have been prepared with varying degrees of success via base-catalyzed routes, the preparation of cyclic poly(organohydrosiloxanes) via these methods would be unacceptable. The base-catalyzed reaction is constrained by the potentially violent reaction of poly(organohydrosiloxanes) with alkali metal compounds and the formation of higher molecular weight gels through silicon-oxygen-silicon bond formation.

Alternatively, cyclic siloxanes have been prepared by the acid-catalyzed depolymerization of linear siloxanes. Burkhardt et al., U.S. Pat. No. 4,276,425, describe a process for preparing cyclic poly(dimethylsiloxanes) through the reaction of linear poly(dimethylsiloxanes) with 50–85% aqueous sulfuric acid at 130°–150° C. for 1.5 to 6 hours. The cyclic species and water are recovered by distillation. While an 89% yield of cyclic species is claimed (~3/1 octamethylcyclotetrasiloxane/decamethylcyclopentasiloxane), this process would not be feasible for the large scale production of cyclic organohydrosiloxanes due to the inherent explosive risk of the contact of large amounts of hydrosiloxanes with highly concentrated sulfuric acid. Another drawback is the corrosive nature of the reaction mixture and additional equipment wear associated with the handling of concentrated sulfuric acid solutions.

Cyclic polysiloxanes, including silicon-hydrogen bond-containing cyclics, were prepared by Miller et al., U.S. Pat. No. 3,714,213, using sulfuric acid-treated clay to crack linear poly(methylhydrosiloxanes) in a pot distillation column at ~300° C. While cyclic products were formed, this process would not be commercially viable due to the prolonged exposure of the reactant linear hydrosiloxanes to heat and acidity. The large amounts of evolved hydrogen gas and the loss of yield due to the formation of high molecular weight material would make the scale-up of such a process difficult and potentially dangerous.

Crivello et al., U.S. Pat. No. 4,895,967, disclose the incremental addition of linear polysiloxane, including poly(methylhydrosiloxane), to a hot (200°–800° C.) acid catalyst under reduced pressure. The resultant volatile cyclic compounds are recovered through condensation. Although the semi-batch nature of this process reduces the potential risk of a build-up of linear hydrosiloxanes in contact with heat and acidity, the risk still remains. High molecular weight nonvolatile species will tend to stay on the catalyst surface and gel through silicon hydride dehydrogenation over the course of the reaction, thus deactivating the catalyst surface. This would produce hydrogen and allow the build-up of linear hydrosiloxanes. An additional disadvantage is that the incremental addition of the reactants is an inefficient and costly utilization of reactor volume and catalyst active surface area, since the reactants are not exposed to the entire catalyst bed. Since the residence time on the catalyst is fixed, the flexibility of this process to produce various amounts of different cyclic species is limited.

Processes disclosed up to now for the production of cyclic organohydrosiloxanes have employed process conditions and materials that are costly, potentially hazardous, and offer little flexibility in producing various cyclic species. Therefore, it would be advantageous to provide a process that could produce cyclic hydrosiloxanes and/or cyclic diorganosiloxanes safely and in high yield, with the flexibility to vary the product distribution.

SUMMARY OF THE INVENTION

Figure 1:
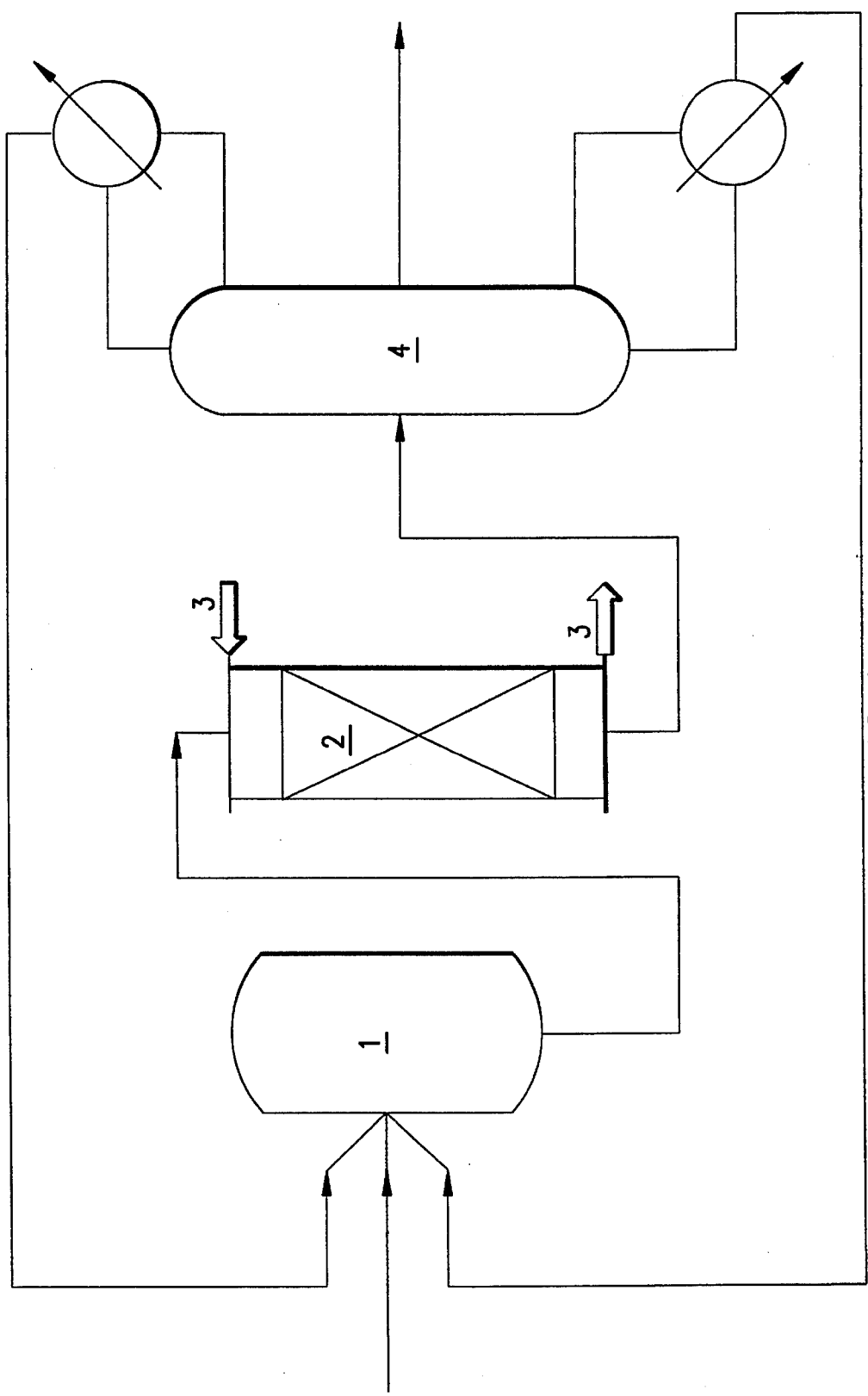
FIG. 1 is a schematic representation of one form of the process of this invention in which a polysiloxane feed is continuously pumped under pressure through a tubular reactor containing a fixed bed of acidic catalyst.

The process of this invention for the production of cyclic polysiloxanes comprises (a) continuously passing a feed comprising linear polysiloxanes through a reactor containing a solid acid catalyst at a pressure greater than 14.7 psi absolute under an inert atmosphere to produce a mixture of volatile cyclic polysiloxanes, nonvolatile reaction products, and unreacted linear polysiloxanes. The volatile products can then be recovered, and the nonvolatile reaction products and unreacted linear polysiloxanes can be added to the linear polysiloxane feed to form a recycle stream that is passed back through the reactor. Recycling increases the yield of the desired cyclic species.

The advantages of this continuous operation over previously used processes include product flexibility and enhanced efficiency and safety. The control of siloxane feed concentration, reactor residence time, and temperature afford great flexibility in tailoring the reaction selectivity and therefore the product composition. Additionally, the contact of potentially dangerous hydrosiloxane with the acidic catalyst at high temperatures is kept to a minimum because of the limited amount of feed material in the reactor at any one time. The flowing of an inert gas through the catalyst bed also keeps the concentration of any hydrogen gas formed in the reaction low. Since the process of the present invention is not necessarily constrained by equilibrium, the process conditions can be varied to enhance the selectivity for a particular cyclic species. The resultant cyclic siloxanes can be used for the preparation of organosilicon polymers.

DETAILED DESCRIPTION OF THE INVENTION

A schematic representation of one form of the process that can be employed in the practice of the present invention is shown in FIG. 1. In (1), a mixing reservoir, the polysiloxane raw material is mixed with any material from the distillation column that is to be recycled back to the reactor. The material from this tank constitutes the feed, and is pumped continuously to the tubular reactor (2), which is packed with a solid acidic catalyst. Nitrogen gas (3) is used as the inert gas and is also passed through the reactor. The products of the reaction are then sent to a distillation column (4) where the cyclic products of interest are recovered.

The unreacted and partially reacted linear siloxanes and the undesired cyclic compounds are recycled back to the feed reservoir (1), where they can be mixed with additional polysiloxane starting material and sent back through the reactor.

The polysiloxane starting material for the process of this invention comprise linear poly(diorganosiloxanes); linear poly(organohydrosiloxanes), or mixtures thereof. Suitable polysiloxane starting materials include, for example, poly(dimethylsiloxanes), poly(methylhydrosiloxanes), poly(methylethylsiloxanes), poly(methylphenylsiloxanes), poly(phenylhydrosiloxanes), poly(diphenylsiloxanes), a copolymer of dimethylsiloxane and methylhydrosiloxane, and a copolymer of methylphenylsiloxane and dimethylsiloxane. The length of the siloxane chain is not critical. Typically such a siloxane will contain between 3 and 40 siloxane units. There is no theoretical upper limit to the molecular weight of the feed material, as long as the polysiloxane can be pumped through the heated catalyst bed. Alternatively, high molecular weight polysiloxanes can be dissolved in a solvent before introducing them into the reactor. Such a solvent should have a boiling point above that of the cyclic polysiloxanes that are produced.

A reactor system is employed consisting of a column that is heated to allow the temperature to be varied, e.g., by placing in a furnace, or by fitting with a jacket through which flows a heat transfer fluid. The reactor is packed in the inlet region with an inert material, such as, for example, stainless steel beads. This inlet region will typically extend about 1/16 to about 1/8 of the entire length of the reactor. However, the exact length is not critical. This region acts to pre-heat the reactant polysiloxane stream prior to contacting the solid acid catalyst. The remainder of the reactor is packed with the catalyst. The length of the reactor is such that it is preferably greater than about 20 times the diameter of the reactor, although the length may be as low as about 10 times the reactor diameter. Typically the reactor temperature is held between about 25° and about 800° C. However the reaction can be run at temperatures between about 200° and about 600° C., preferably about 300° to about 375° C., depending on the activity of the solid acid catalyst employed. The pressure of the reactor is generally held between about 15 psi and about 29.4 psi absolute, preferably about 15 to about 17 psi absolute. However, lower or higher pressures can be employed if desired to alter the cyclic siloxane product distribution.

Prior to the introduction of the polysiloxane to the catalyst bed, the catalyst should preferably be thermally treated at a temperature above which the cracking reaction is to take place, the minimum temperature being about 100° C. This catalyst pretreatment is preferred to remove any bound water from the catalyst surface. Catalyst pretreatment is strongly recommended, since the presence of water on the catalyst surface could lead to undesired side reactions with the polysiloxane feed, by which hydrogen gas and higher molecular weight siloxane species are produced. These higher molecular weight species could cause gelation and plugging of the catalyst bed. This treatment involves the heating of the catalyst bed to the desired temperature in flowing inert gas, and holding for a period sufficient to remove the bound water. The time required is typically between about 0.5 and about 2 hours, but can vary depending on the nature and condition of the catalyst.

Typically the process stream is introduced at pressures of about 15.5 to about 29.4 psi absolute. The linear polysiloxanes are introduced to the reactor under pressure so that the fixed bed is filled with the process stream, and the process stream contacts the fixed bed of catalyst in a continuous fashion along the length of the bed. Pressure greater than atmospheric is needed for the process stream to travel through the length of the reactor. Increasing the pressure of the process stream over the fixed bed increases the throughput rate of the process stream and decreases the volatility of the products. The product formed along the catalyst bed comprises cyclic polysiloxanes and lower poly(organosiloxanes).

The polysiloxane starting material is pumped continuously through the reactor along with an inert gas, which is used to blanket the reactor to exclude oxygen. Prior to being fed to the reactor, the inert gas is purified by flowing through an appropriate medium to remove substantially all traces of oxygen and water. The flow of polysiloxane is such that the liquid hourly space velocity (LHSV) is between about 0.5 and about 10 $hr^{-1}$, preferably between about 1 and about 4 $hr^{-1}$, and most preferably about 3 $hr^{-1}$. The rate of flow of the inert gas is not critical. However, it should be high enough so that the cyclic products are continually swept from the reactor. Typically the gas hourly space velocity (GHSV) is between about 100 and about 400 $hr^{-1}$, although higher or lower values can be used. The preferred inert gas is nitrogen. However, other inert gases such as argon and helium can also be used.

The preferred solid acid catalyst is an acidic zeolite, such as an HY or other acidic zeolite molecular sieve with a pore size of about 5 to about 20 angstroms. However, other solid acids, such as a supported mineral acid catalyst, silica-alumina, titano-silica-alumina, ion exchange resins, acid-treated clay, or the class of solid acids known as heteropolyacids can also be used as the catalyst. The catalyst should preferably be in a form, such as pellets or extrudates, that can be packed into a reactor and allow the reactant polysiloxane to flow through the catalyst bed.

Although the preceding discussion has referred to the use of a reactor containing a fixed bed of solid acid catalyst, the process could also be carried out using a fluidized bed system under the appropriate conditions.

The volatile cyclic siloxane products are recovered, preferably by distillation. The distillation conditions should be such that only the cyclic components of interest are distilled out of the product mixture. Prior to distillation, the product mixture consists of a distribution of cyclic polysiloxanes, a distribution of partially reacted linear polysiloxanes, and unreacted polysiloxane feed. Following distillation, the unreacted and partially reacted polysiloxanes, as well as any undesired cyclic components, can be recycled, mixed with fresh linear polysiloxane feed material and subsequently passed back through the reactor to give additional cyclic species of interest. By varying the ratio of feed to recycle along with the reactor residence time, the product composition can be directed toward certain cyclic species, for example, the enhancement of the cyclic siloxane trimer versus the tetramer.

In a preferred embodiment, the linear polysiloxane feed comprises linear poly(methylhydrosiloxanes), and the product stream before distillation comprises a mixture of trimethylcyclotrisiloxane, tetramethylcyclotetrasiloxane, pentamethylcyclopentasiloxane, and hexamethylcyclohexasiloxane. After distillation, the product stream would comprise cyclic siloxanes having 4–5 organosiloxy units. Material containing three organosiloxy units (as overheads) and material containing more than 4–5 organosiloxy units (as bottoms) would be added to the incoming feedstream to the reactor so that greater than 80% conversion to the desired product is obtained.

In the following examples, the percentage of each type of cyclic polysiloxane is given for the reaction product before distillation. The distillation conditions needed for the recovery of the various cyclic polysiloxanes can easily be determined by one skilled in the art.

EXAMPLE 1

A ¾ (outside diameter) stainless steel tubular reactor was packed with 40 g of Valfor CBV 3062 molecular sieve catalyst (1/16 diameter extrudates; $SiO_2/Al_2O_3=36$; 5 Angstrom average pore diameter), available from PQ corporation, Valley Forge, Pa., U.S.A. The reactor was placed in a furnace and flowing nitrogen was introduced at a gas hourly space velocity (GHSV) of ~1000 $hr^{-1}$. The reactor was heated in flowing nitrogen to a temperature of 450° C. for 4 hours to remove substantially all bound water from the catalyst surface. Following the catalyst pretreatment, the temperature was decreased to 270° C. in flowing nitrogen. Linear hydrosiloxane fluid 1107 was then pumped through the catalyst bed continuously at a liquid hourly space velocity (LHSV) of 2 $hr^{-1}$. The hydrosiloxane fluid comprises poly(methylhydrosiloxanes), had a number average molecular weight of 1200, was endcapped with trimethylsiloxane, and is available from Dow Corning, Midland, Mich., U.S.A. The reactor pressure increased from atmospheric pressure to ~2 psig. A total of 266 g of linear polysiloxane was fed to the reactor. A condenser placed downstream from the reactor was used to collect the product. The volatile products were isolated from the product mixture by flash distillation at 130° C. and 2 Torr. Volatile products (205 g) were isolated for a yield of 77%, based on the weight of linear poly(methylhydrosiloxanes) fed to the reactor. The volatile products were analyzed by gas chromatography. The major reaction products were cyclic poly(hydrosiloxanes), mainly those containing 3–6 siloxane units. The volatile product stream consisted of 8.4% trimethylcyclotrisiloxane, 39.9% tetramethylcyclotetrasiloxane, 28.3% pentamethylcyclopentasiloxane, and 11.9% hexamethylcyclohexasiloxane, with the remainder primarily consisting of larger ring cyclic hydrosiloxanes.

EXAMPLE 2

The reaction of Example 1 was repeated except that the linear poly(hydrosiloxane) flow was increased to a LHSV of 4 $hr^{-1}$. A total of 327 g of the linear poly(methylhydrosiloxanes) were fed to the reactor. The product was collected and isolated as above. Volatile products (132 g) were recovered for a yield of 40.4%. Gas chromatography analysis showed 5.3% trimethylcyclotrisiloxane, 38.0% tetramethylcyclotetrasiloxane, 29.2% pentamethylcyclopentasiloxane, and 12.2 hexamethylcyclohexasiloxane. The decrease in residence time resulted in decreased selectivity toward trimethylcyclotrisiloxane.

EXAMPLE 3

The procedure of Example 1 was repeated with the exception that the LHSV was held at 3 $hr^{-1}$, and the temperature was varied between 250° and 285° C. The following table shows the volatile product yield (isolated by flash distillation at 130° C. and 2 torr) and composition in percent as the temperature of the reaction was varied.

TABLE 1

|  | 250° C. | 270° C. | 285° C. |
| --- | --- | --- | --- |
| % Volatile product yield | 56.4 | 67.7 | 76.9 |
| % Trimethylcyclotrisiloxane | 3.1 | 5.6 | 7.6 |
| % Tetramethylcyclotetrasiloxane | 37.2 | 36.4 | 37.4 |
| % Pentamethylcyclopentasiloxane | 31.2 | 27.4 | 27.4 |
| % Hexamethylcyclohexasiloxane | 13.4 | 11.6 | 11.5 |

EXAMPLE 4

After the volatile material produced at 270° C. above in Example 3 was isolated from the reaction products, 237 g of the remainder, which consisted of unreacted linear hydrosiloxane feed and partially converted nonvolatile products, was recycled back through the reactor at 270° C. and a LHSV of 3 $hr^{-1}$. The output from the reactor was collected by a condenser and the product mixture was flash distilled as above. Volatile products (182 g) were isolated corresponding to a yield of 76.7%, based on the total recycle fed to the reactor. The two-pass yield of volatile products was 92.4%. Gas chromatography analysis of the second pass-through product showed 4.4% trimethylcyclotrisiloxane, 29.8% tetramethylcyclotetrasiloxane, 20.4% pentamethylcyclopentasiloxane, and 8.0% hexamethylcyclohexasiloxane.

EXAMPLE 5

The reactor described in Example 1 was packed with 21 g of YZ-82 zeolite Y catalyst (1/16 " diameter extrudates; $SiO_2/Al_2O_3=4$; 7.5 Angstrom average pore diameter), available from UOP Corp., Chicago, Ill., U.S.A. The reactor was heated to 285° C. in flowing nitrogen (GHSV=1500 $hr^{-1}$). Linear hydrosiloxane fluid 1107, available from Dow Corning, Midland, Mich., U.S.A. was then fed to the reactor continuously at a LHSV of 2 $hr^{-1}$ for a total of 160 hours. The effluent from the reactor was recovered by a condenser placed downstream from the reactor. A sample of the product mixture was taken between approximately 12.5 and 22 hours onstream, flash distilled to recover the volatile products, and analyzed by gas chromatography. A total of 381 g of feed was introduced into the reactor over this time period. A total of 241 g of volatile products was recovered for a yield of 63.2%. The analysis of the volatile products showed 11.9% trimethylcyclotrisiloxane, 33.7% tetramethylcyclotetrasiloxane, 23.1% pentamethyl-cyclopentasiloxane, and 10.2% hexamethylcyclohexasiloxane. A further sample was recovered between 152 and 160 hours onstream. A total of 357 g of linear poly(hydrosiloxanes) was introduced to the reactor, and a total of 228 g of volatile products was recovered for a yield of 63.9%. The analysis of this product showed 13.6% trimethylcyclo-trisiloxane, 34.3% tetramethylcyclotetrasiloxane, 23.3% pentamethylcyclopentasiloxane, and 10.1% hexamethylcyclo-hexasiloxane.

It is not intended that the examples given here should be construed to limit the invention, but rather they are submitted to illustrate some of the specific embodiments of the invention. Various modifications and variations of the present invention can be made without departing from the scope of the appended claims.

I claim:

1. A process for the production of cyclic polysiloxanes, comprising
    (a) continuously passing a feed comprising linear polysiloxanes through a reactor containing a solid acid catalyst at a pressure greater than 14.7 psi absolute under an inert atmosphere, and
    (b) recovering a mixture comprising volatile cyclic polysiloxanes, nonvolatile reaction products, and unreacted linear polysiloxanes.

2. The process of claim 1, which additionally comprises (c) recovering volatile products from the mixture in step (b), and
    (d) adding the nonvolatile reaction products and unreacted linear polysiloxanes to the polysiloxane feed to form a recycle stream that is passed back through the reactor.

3. The process of claim 1, wherein the reactor contains a fixed bed of the solid acid catalyst.

4. The process of claim 3, wherein the polysiloxane feed is passed through the reactor at a liquid hourly space velocity of about 0.50 $hr^{-1}$ to about 10 $hr^{-1}$.

5. The process of claim 4, wherein the liquid hourly space velocity is about 1 to about 4 $hr^{-1}$.

6. The process of claim 5, wherein the liquid hourly space velocity is about 3 $hr^{-1}$.

7. The process of claim 3, wherein step (a) is carried out at a temperature of about 25° to about 800° C.

8. The process of claim 7, wherein the temperature is about 200° to about 600° C.

9. The process of claim 8, wherein the temperature is about 300° to about 375° C.

10. The process of claim 3, wherein the pressure is about 15.0 to about 29.4 psi absolute.

11. The process of claim 10 wherein the pressure is about 15 to about 17 psi absolute.

12. The process of claim 1, wherein the polysiloxane feed comprises linear polysiloxanes selected from the group consisting of linear poly(diorganosiloxanes), linear poly(organohydrosiloxanes), and mixtures thereof.

13. The process of claim 12, wherein the polysiloxane feed comprises linear poly(diorganosiloxanes).

14. The process of claim 13, wherein the linear poly(diorganosiloxanes) comprise poly(dimethylsiloxanes).

15. The process of claim 13, wherein the linear poly(diorganosiloxanes) comprise poly (methylphenylsiloxanes).

16. The process of claim 12, wherein the polysiloxane feed comprises linear poly(organohydrosiloxanes).

17. The process of claim 16, wherein the linear poly(organohydrosiloxanes) comprise poly (methylhydrosiloxanes).

18. The process of claim 1, wherein the polysiloxane feed comprises a copolymer of a diorganosiloxane and an organohydrosiloxane.

19. The process of claim 18, wherein the polysiloxane feed comprises a copolymer of methylphenylsiloxane and dimethylsiloxane.

20. The process of claim 18, wherein the copolymer comprises a copolymer of dimethylsiloxane and methylhydrosiloxane.

21. The process of claim 1, wherein the polysiloxane feed comprises a mixture of linear polysiloxanes and cyclic polysiloxanes.

22. The process of claim 21, wherein the cyclic polysiloxanes are selected from the group consisting of poly(diorganocyclosiloxanes), poly(organohydrocyclosiloxanes), and mixtures thereof.

23. The process of claim 22, wherein the cyclic polysiloxanes comprise poly(organohydrocyclosiloxanes).

24. The process of claim 23, wherein the poly(organohydrocyclosiloxanes) comprise poly(methylhydrocyclosiloxanes).

25. The process of claim 24, wherein the poly(methylhydrocyclosiloxanes) are selected from the group consisting of trimethylcyclotrisiloxane, tetramethylcyclotetrasiloxane, pentamethylcyclopentasiloxane, hexamethylcyclohexasiloxane, and mixtures thereof.

26. The process of claim 22, wherein the cyclic polysiloxanes comprise poly(diorganocyclosiloxanes).

27. The process of claim 26, wherein the poly(diorganocyclosiloxanes) comprise poly (dimethylcyclosiloxanes).

28. The process of claim 1, wherein the solid acid catalyst is selected from the group consisting of silicaalumina, titano-silica-alumina, heteropolyacid, supported mineral acid, ion exchange resin, and acidic zeolite catalysts.

29. The process of claim 28, wherein the solid acid catalyst is silica-alumina.

30. The process of claim 28, wherein the solid acid catalyst is titano-silica-alumina.

31. The process of claim 28, wherein the solid acid catalyst is a heteropolyacid catalyst.

32. The process of claim 28, wherein the solid acid catalyst is a supported mineral acid catalyst.

33. The process of claim 28, wherein the solid acid catalyst is an ion exchange resin catalyst.

34. The process of claim 28, wherein the solid acid catalyst is an acidic zeolite catalyst.

35. The process of claim 34, wherein the zeolite catalyst is an HY type zeolite.

36. The process of claim 2, wherein the polysiloxane feed comprises poly(organohydrosiloxanes), the reactor contains a fixed bed of the solid acid catalyst, the liquid hourly space velocity is about 1 to about 4 $hr^{-1}$, the temperature is about 200° to about 600° C., the pressure is about 15 to about 29.4 psi absolute, the catalyst is an acidic zeolite catalyst, and the volatile products recovered are poly(organohydrotetra- and -pentacyclosiloxanes).

37. The process of claim 2, wherein the polysiloxane feed comprises poly(methylhydrosiloxanes), the reactor contains a fixed bed of the solid acid catalyst, the liquid hourly space velocity is about 3 $hr^{-1}$, the temperature is about 300° to about 375° C., the pressure is about 15 to about 17 psi absolute, the catalyst is an HY type zeolite catalyst, and the volatile products recovered are tetramethylcyclotetrasiloxane and pentamethylcyclopentasiloxane.

* * * * *